(12) United States Patent
Kesaniemi

(10) Patent No.: US 10,194,817 B2
(45) Date of Patent: Feb. 5, 2019

(54) METHOD AND SYSTEM OF MONITORING CARDIAC FUNCTION BASED ON PATIENT POSITION

(71) Applicant: General Electric Company, Schenectady, NY (US)

(72) Inventor: Martti Ilmari Kesaniemi, Helsinki (FI)

(73) Assignee: General Electric Company, Schnectady, NY (US)

( * ) Notice: Subject to any disclaimer, the term of this patent is extended or adjusted under 35 U.S.C. 154(b) by 0 days.

(21) Appl. No.: 15/940,606

(22) Filed: Mar. 29, 2018

(65) Prior Publication Data

US 2018/0220909 A1    Aug. 9, 2018

Related U.S. Application Data

(63) Continuation of application No. 15/041,221, filed on Feb. 11, 2016, now Pat. No. 9,955,884.

(51) Int. Cl.
| | |
|---|---|
| *A61N 5/04* | (2006.01) |
| *A61B 5/0402* | (2006.01) |
| *A61B 5/00* | (2006.01) |
| *A61B 5/04* | (2006.01) |
| *A61B 5/11* | (2006.01) |
| *G06F 19/00* | (2018.01) |

(52) U.S. Cl.
CPC ........ *A61B 5/0402* (2013.01); *A61B 5/04012* (2013.01); *A61B 5/1116* (2013.01); *A61B 5/721* (2013.01); *A61B 5/746* (2013.01); *G06F 19/00* (2013.01)

(58) Field of Classification Search
CPC .............................. A61B 5/0402; A61B 5/721
See application file for complete search history.

(56) References Cited

U.S. PATENT DOCUMENTS

| | | |
|---|---|---|
| 5,697,374 A | 12/1997 | Odagiri et al. |
| 9,095,316 B2 | 8/2015 | Welch et al. |
| 2012/0029300 A1 | 2/2012 | Paquet |

FOREIGN PATENT DOCUMENTS

EP    2832289    2/2015

*Primary Examiner* — Amanda Hulbert
(74) *Attorney, Agent, or Firm* — Andrus Intellectual Property Law, LLP

(57) ABSTRACT

A method of monitoring the cardiac function of a patient includes receiving a position input from a position sensor attached to the patient and classifying the position input into a position class. Cardiac waveform data is received for the patient and then the cardiac waveform data is compared to model waveform parameters for the position class.

20 Claims, 5 Drawing Sheets

METHOD AND SYSTEM OF MONITORING CARDIAC FUNCTION BASED ON PATIENT POSITION

CROSS REFERENCE TO RELATED APPLICATION

This application is a continuation of U.S. patent application Ser. No. 15/041,221, filed Feb. 11, 2016, which is incorporated herein by reference in entirety.

BACKGROUND

Cardiac waveforms, such as those measured by electrocardiograph (ECG) monitors, vary with body position changes by the patient. Such variation in cardiac waveforms due to changes in patient position are a common source of problems in cardiac monitoring, including triggering false alarms. For example, changes in a patient's position may cause changes in the QRS and/or ST-T waveforms that are significant enough to trigger a false alarm by an ECG monitor.

SUMMARY

The present disclosure generally relates to a method and system of monitoring cardiac function based on patient position.

One embodiment of a method of monitoring the cardiac function of a patient includes receiving a position input from a position sensor attached to the patient and classifying the position input into a position class. Cardiac waveform data is received for the patient and then the cardiac waveform data is compared to model waveform parameters for the position class.

One embodiment of a system for monitoring cardiac function of a patient includes an electrocardiograph monitor configured to record cardiac waveform data from the patient and at least one position sensor configured to sense a position of the patient and produce a position input. The system further includes a processor, a position analysis module, and a waveform analysis module. The position analysis module is executable on the processor to receive the position input, determine a position class, wherein the position class is one of a predefined set of position classes, and output the position class. The waveform analysis module is executable on the processor to receive the cardiac waveform data and the position class, compare the cardiac waveform data to model waveform parameters for the position class to determine a cardiac status of the patient, and output the cardiac status.

One embodiment of a non-transitory computer-readable medium having computer executable instructions stored thereon has instructions including the steps of receiving a position input from a position sensor attached to the patient, classifying the position input into a position class, wherein the position class is one of a predefined set of position classes, receiving cardiac waveform data for the patient, and comparing the cardiac waveform data to model waveform parameters for the position class.

BRIEF DESCRIPTION OF THE DRAWINGS

The drawings illustrate the best mode presently contemplated of carrying out the disclosure. In the drawings.

DETAILED DESCRIPTION

The present disclosure was developed in view of the inventor's recognition of the problems posed by changes in cardiac waveforms resulting from changes in patient position. Through experimentation and research in the relevant field, the present inventor recognized that by tracking patient position, current QRS, ST-T, and other ECG parameter values can be compared to those recorded earlier when the patient was in the same position, instead of comparing the current cardiac waveform values to values measured when the patient was in a different position. The cardiac waveforms may be associated with a position class based on patient position measured by a position sensor at the time of the waveform recording. Model waveform parameters may be established for each position class based on the cardiac waveform data recorded from the patient while the patient was in a position that falls within that position class. The model waveform parameters for that position class may then be used as a baseline for comparison to subsequently recorded cardiac waveform data measured from the patient when the patient returns to a position in that position class.

Figure 1:
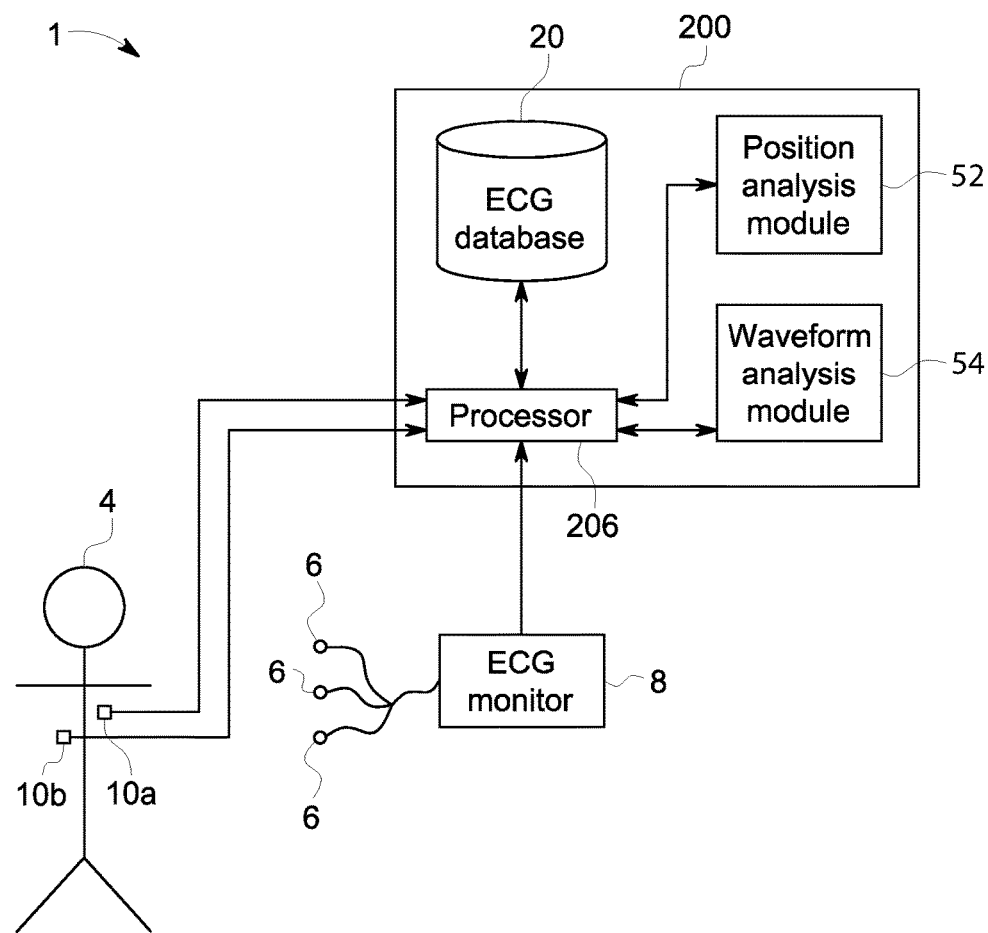
FIG. 1 is a schematic diagram of one embodiment of a system for monitoring cardiac function of a patient.

FIG. 1 depicts one embodiment of a system 1 of monitoring cardiac function of a patient. The system 1 includes an electrocardiograph (see ECG) monitor 8 that records cardiac waveform data 32 (also see FIG. 4) from the patient 4 via electrodes 6. The ECG monitor 8 may be any type of electrocardiograph monitor, which may be a traditional wired ECG monitor or a wireless ECG monitor. The system 1 for monitoring cardiac function of the patient 4 further includes two position sensors 10a and 10b attached to the torso of the patient 4. The ECG monitor 8 and the position sensors 10a and 10b communicate with the computing system 200, and specifically with the processor 206 of the computing system 200. The computing system 200 also includes a position analysis module 52 executable on the processor 206 to receive position input information from the position sensors 10a and 10b and determine a position class based on the position input from the position sensors 10a and 10b. The computing system 200 further includes a waveform analysis module 54 that is executable on the processor 206 to receive the cardiac waveform data 32 from the ECG monitor 8 and compare the cardiac waveform data 32 to model waveform parameters for the position class determined by the position analysis module 52 to determine a cardiac status of the patient. For example, the cardiac status may provide a classification of the cardiac waveform data 32 recorded from the patient on a continuum between healthy and a critical alarm status, according to criteria known and available in the art for classifying cardia condition based on recorded ECG waveforms. The waveform analysis module 54 may further be executable on the processor 206 in order to access and store information in an ECG database 20. For example, the waveform analysis module 54 may be executable to determine whether model waveform parameters exists for a particular position class identified by the position analysis module 52. If such model waveform parameters do not exist for a particular position class, then the waveform analysis module 54 may establish new model waveform parameters for that position class, as is explained further herein. The model waveform parameters established by the waveform analysis module 54 may be stored in ECG database 20 and accessed any time that the patient 4 enters the relevant position class. Other information and output developed by the waveform analysis module 54 executed on the processor 206 may also be stored in the ECG database 20, including the cardiac status of the patient Likewise, the position analysis module 52 may be executable on the processor 206 to access information stored in the ECG database 20 and/or may be executable to store the determined position class in the ECG database 20. In other embodiments, the model waveform parameters for the position classes may be stored in local memory dedicated and/or accessible to the processor 206 executing the position analysis module 52 and waveform analysis module 54.

FIGS. 2A-2D depict various patient positions that may exemplify various predefined position classes. In the Figures, the patient 4 has a position sensor 10 on their torso, and specifically placed in the midsection of the patient's chest approximately at the location of the heart. In other embodiments, the position sensor 10 may be placed at another location on the patient's chest, such as higher up on the patient's chest, on the patient's abdomen, on the patient's side, etc. In still other embodiments, two or more position sensors may be utilized, an example of which is depicted in FIG. 1. When more than one position sensor 10 is utilized, multiple position sensors may be placed on the patient's torso, such as to provide better ability to eliminate measurement results that do not indicate the orientation accurately from any one position sensor. For example, accelerometers are often prone to detect the acceleration caused by a moving patient, such as changing position or walking, for example, and these accelerations hide the orientation information of the sensor. Multiple position sensors may be utilized to eliminate the ambiguity of the position caused by the accelerations created through patient movement. For example, the output of each of the multiple position sensors may be compared to find commonalities in sensed position, increasing the likelihood that the output is a measurement of patient position rather than noise. For example, when having an accelerometer positioned to the right-hand side of the patient's chest, if the patient moves his right arm while conducting an activity, such as eating, this sensor is likely to catch the accelerations caused by the hand movement, and the patient orientation becomes ambiguous. In there is another accelerometer attached to the left-hand side of the patient's chest, this accelerometer is less prone to the movement accelerations, and the patient position can be detected by using the signal of the second accelerometer. Further, the problem of such movement "artefacts" or ambiguity may be solved by using a combined gyroscope-accelerometer as the orientation sensor, which allows movement tracking even during motion.

In other embodiments were multiple position sensors are present, one or more of the sensors may be placed on areas of the patient other than the patient's torso, such as on the patient's arms or legs. This can provide detailed position information that may be used to define very precise position classes, and thus provide very precise waveform data modeling, where model waveform parameters are stored for each of the precise position classes. For example, the placement of a patient's arms when a patient is laying supine, or when lying on their side, may impact the ECG recorded from the patient. Accordingly, in some embodiments it may be desirable to place a position sensor 10 on each of the patient's arms so that arm position can be accounted for in the position classes. The motion sensor(s) 10 may be attached to the patient by any suitable means, such as attached to the patient 4 by any suitable means, such as attached to the patient's skin by tape or pressed against the patient's skin by a band or by form-fitting clothing.

The position sensor(s) 10 may be any sensor capable of providing an output relevant to motion and/or position of the patient. In one embodiment, the position sensor 10 is an accelerometer, such as a three-axis accelerometer. In other embodiments, the position sensor(s) 10 may be a gyroscope, such as a three-axis gyroscope, or may be a combination accelerometer/gyroscope sensor. In still other embodiments, the position sensor(s) 10 may be another type of inertial sensor, such as a combination accelerometer and/or gyroscope further including a magnetometer. In still other embodiments, the position sensor 10 may be a sensor capable of acting as an accelerometer and a gyroscope.

Figure 2A:
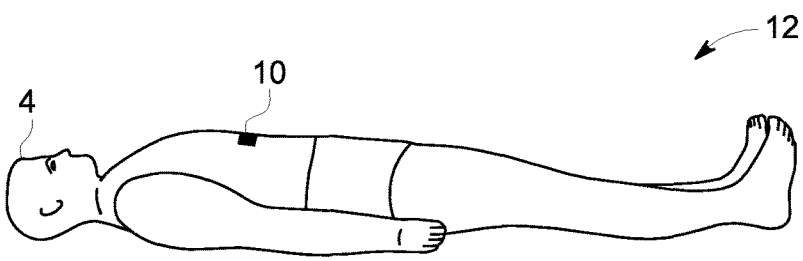
FIGS. 2A-2D depict various patient positions exemplifying position classes.
Figure 2B:
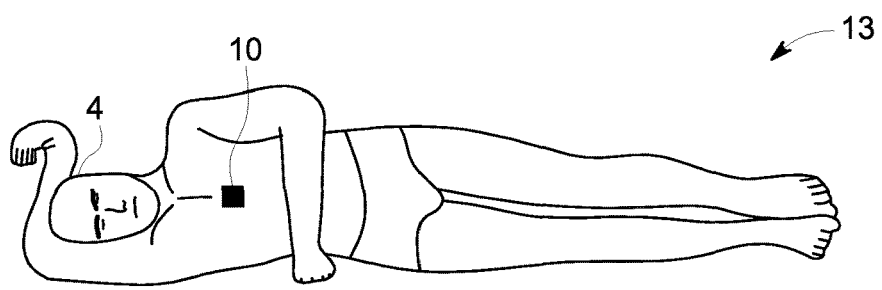
Figure 2C:
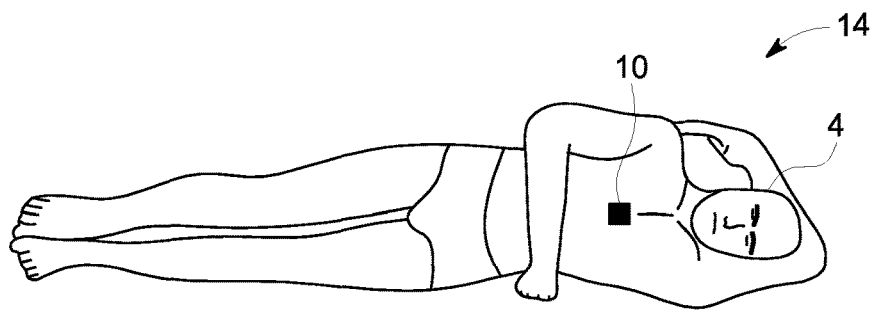
Figure 2D:
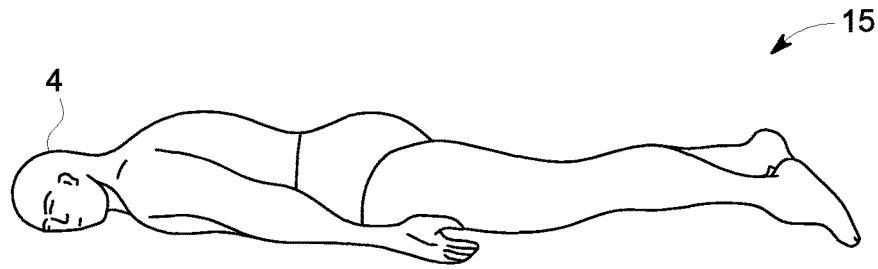

In FIG. 2A, the patient 4 is depicted in a supine position 12, which may form one exemplary position class. FIG. 2B depicts the patient 4 in a right horizontal position 13, and FIG. 2C depicts the patient 4 in a left horizontal position 14. FIG. 2D depicts the patient 4 in a prone position 15. Each of the depicted positions 12-15 may exemplify a predefined position class for which model waveform parameters are established and stored for the patient 4. Accordingly, the position analysis module 52 may receive position input from the position sensor 10 and classify the patient position into one of the supine position 12, the right side position 13, the left side position 14, or the prone position 15. The position class determined by the position analysis module 52 may then be used by the waveform analysis module 54 to select the appropriate model waveform parameters for use in assessing the cardiac status of the patient 4.

Figure 3A:
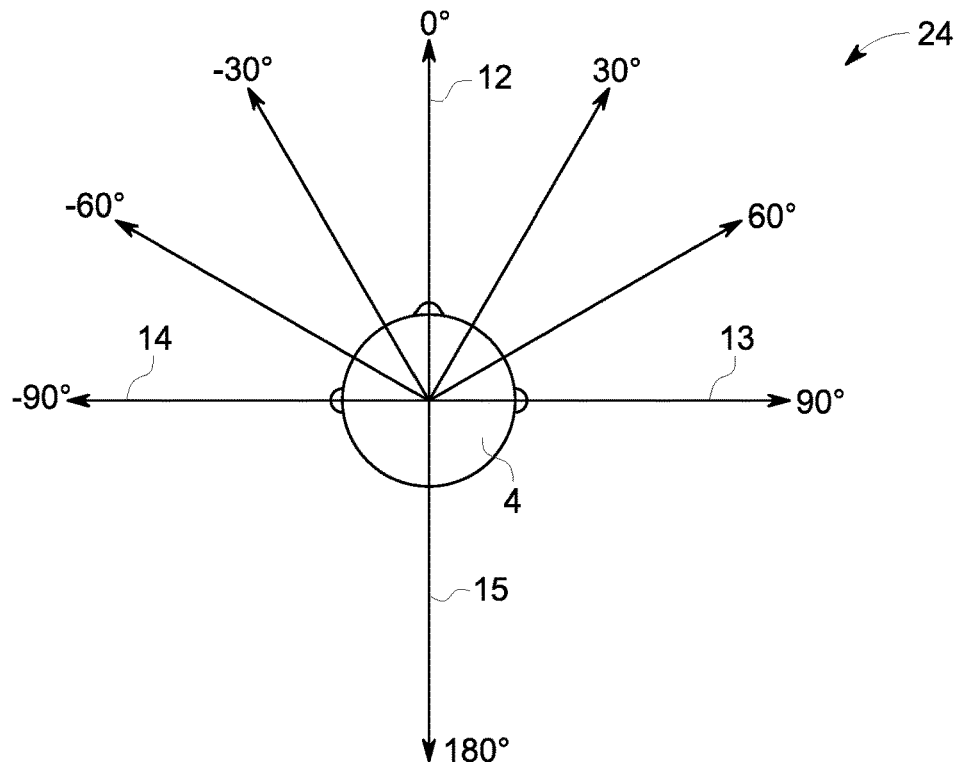
FIGS. 3A and 3B graphically depict various position classifications.
Figure 3B:
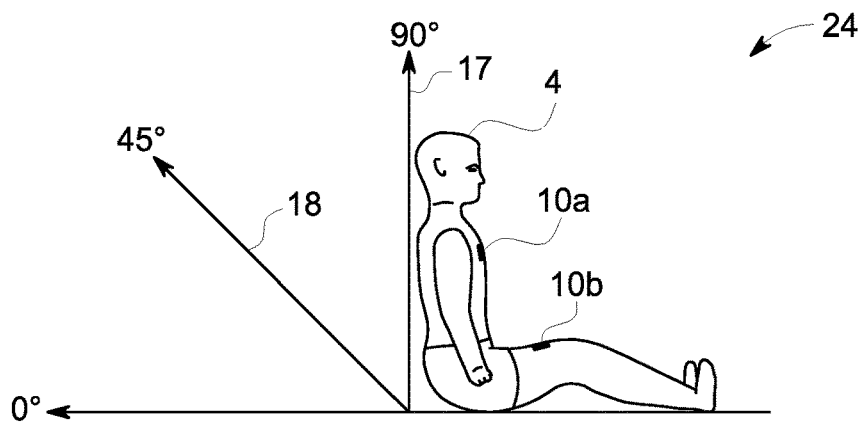

FIGS. 3A and 3B depict an embodiment of a system 1 having a predefined set of position classes 24 that include a set of horizontal positions depicted in FIG. 3A and a set of vertical positions depicted in FIG. 3B. The horizontal positions in the predefined set of position classes 24 include six position classes between the right side horizontal position 13 and the left side horizontal position 14. A seventh position class is defined as the prone position class 15. Specifically, a position class is defined at every 30° increment between the right side horizontal position class 13 labeled as 90°, the supine position class 12 labeled as 0°, and the left side horizontal position class 14 labeled as −90°.

In FIG. 3B, the exemplary embodiment of vertical position classes included in the predefined set of position classes 24 include a vertical position 17, where the patient's torso is in an upright position at or near 90° from horizontal. As explained below, the system may or may not be configured to differentiate between standing and sitting vertical positions, which may depend on the sensor configuration. The exemplary predefined set of position classes 24 further includes a reclined position 18 where the patient's torso is at a 45° angle between the vertical position 17 and a fully horizontal position where the patient is laying down, which could take the form of any of the positions depicted in FIG. 3A. In other embodiments, a greater or lesser number of predefined position classes may be included in the predefined set of position classes 24. Further, the positions may be divided in equal increments, like the depicted embodiment, or may be defined on another basis. For example, the predefined set of position classes 24 may include common positions, such as positions most preferred by patients or common hospital bed settings. Alternatively or additionally, the predefined set of position classes 24 may include expected positions for the patient, such as based on the patient medical history and/or the patient condition. For example, certain positions may be advised or preferred for patients recovering from particular procedures.

The position class may be selected from a predefined set of position classes. In various embodiments, the predefined set of position classes may include any number of positions. In one embodiment, the predefined set of position classes may be those position classes 12-15 exemplified in FIGS. 2A-2D. In other embodiments, more or less position classes may be defined between the right side horizontal and the left side horizontal. The position classes may also include various vertically differentiating classes, such a vertical seated position, a standing position, and/or the position classes exemplified in FIG. 3B. In embodiments differentiating between a vertical seated position and a vertical standing position, it may be beneficial to use more than one position sensor 10, with at least one position sensor placed on the patient's torso and another placed on at least one of the patient's legs, such as on their thigh. FIG. 3B depicts an example arrangement of two position sensors 10a and 10b, where position sensor 10a is placed on the patient's torso and position sensor 10b is placed on one of the patient's thighs. Thus, when the patient is in a seated position the position sensor 10a may detect a vertical, upright position while the position sensor 10b detects a horizontal position. When the patient is in a standing position, both position sensors 10a and 10b detect a vertical position, then appropriate model waveform parameters for the standing position class can be used. Furthermore, the position sensor arrangement may be utilized to detect when the patient is walking, for example, by detecting certain continuous motion patterns in the motion sensors 10a, 10b, especially in the motion sensor 10b on the patient's legs. Then, the model waveform parameters for the walking position class could then be used.

The position analysis module 52 determines the position class based on the position input 30, which is the output of the position sensor(s) 10. For example, the position input 30 may be classified into one of the predefined set of position classes 24 depicted in FIGS. 3A and 3B by selecting the position class closest to the position input 30 value detected by the position sensor 10. To provide an explanatory example, if the position input 30 from the position sensor 10 is horizontal at 10° (toward the right horizontal position), then the position analysis module 52 may classify the position input as being in the supine position class 12 because the supine position class 12 is the closest to the measured position input. In another embodiment, when the patient position falls between two adjacent position classes, the model waveform parameters for each of the two surrounding position classes may be interpolated to create model waveform parameters that are a hybrid of the two surrounding models and better represents the patient's position.

Model waveform parameters may be established for each position class in the predefined set of position classes 24, or at least each position class that the patient enters into for a sufficient period of time such that the model waveform parameters can be established. The model waveform parameters are data establishing a baseline or a normal for the patient at a given position or position class. For example, the model waveform parameters may include a model waveform against which the patient's cardiac waveform data 32 recorded by the ECG monitor 8 can be compared to detect changes in the patient's cardiac status. The model waveform parameters may include an average waveform established by averaging the waveforms classified as belong to that same position class—e.g., a "normal beat" for a certain patient position. These average waveforms for each position class can be gradually updated according to new data recorded in that position class. In certain embodiments, the model waveform parameters may be or may further include waveform parameters computed from the average waveform. In still other embodiments, the model waveform parameters may include a "snippet" of a recorded ECG waveform, which may be filtered to remove noise and/or processed to remove the baseline. Alternatively or additionally, the model waveform parameters may include amplitudes and timing data of the QRS complex and/or the ST-T complex that is normal for that patient given a particular electrode arrangement. If electrode placement is changed, the model waveform parameters may need to be re-established.

In one embodiment, the model waveform parameters are established for each position where the patient 4 remains for a sufficient amount of time for establishment of the model waveform parameters. In such an embodiment, when the patient settles in a new position, the waveform analysis module 54 may determine whether model waveform parameters have been established for the determined position class. If not, the waveform analysis module 54 may establish the model waveform parameters for that position class. The model waveform parameters may be established anew, or may be created by adapting or copying model waveform parameters from another position class, such as the closest position class for which model waveform parameters are established. For example, referring to the example of FIG. 3A, if the position class is determined to be 30°, but no model waveform parameters are available for that position class, the waveform analysis module 54 may adapt the model waveform parameters established for the supine position class 12, utilizing the new cardiac waveform data 32 being recorded from the patient 4 at the 30° position. For example, differences may be identified between the model waveform parameters for the supine position class 12 and the cardiac waveform data 32 being recorded from the patient at 30°, and the model waveform parameters for the position class at 30° will be configured to reflect and include those differences.

In another embodiment, the model waveform parameters may be established for each position class at the outset, such as by having the patient go through a particular series of positions and recording cardiac waveform data at each position in order to establish model waveform parameters at each position.

In order to avoid the problem of false alarms when a patient enters a new position for which model waveform parameters have not been established, alarm conditions may be adjusted. Thus, the system 1 may be configured to conduct an assessment immediately upon a position change by the patient to determine whether appropriate model waveform parameters are available for the position class associated with the patient's new position. If not, the alarm condition thresholds may be adjusted, such as by raising the threshold for an alarm condition until the model waveform parameters can be established for that position class. Thereby, the system 1 can avoid producing false alarms due to changes in waveforms as a result of a position change, rather than as a result of an actual change in the patient's cardiac status. For example, the alarm thresholds may be adjusted to accommodate certain expected changes in ECG waveforms that may be associated with position changes.

Alternatively, the alarm function may be suspended altogether until the new model waveform parameters are established for the position class.

Figure 4:
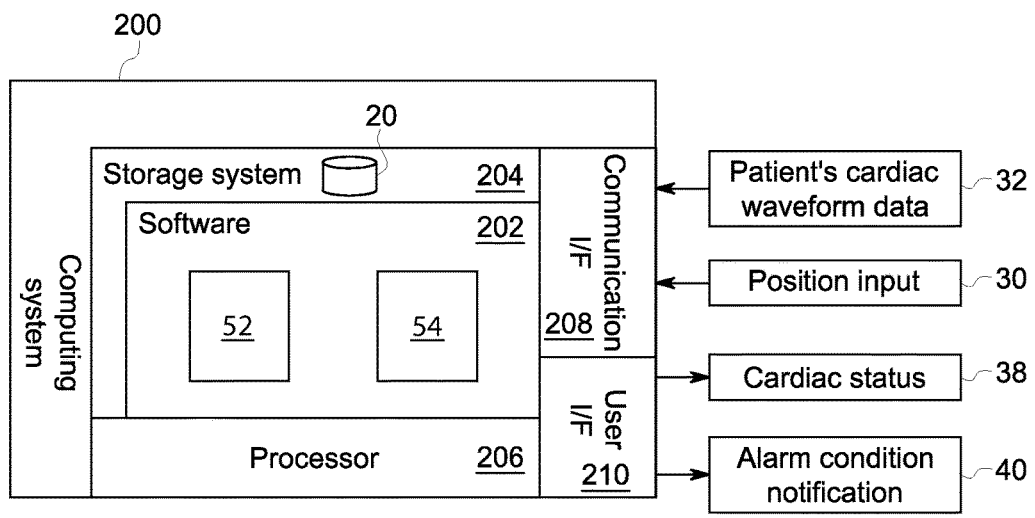
FIG. 4 is a schematic diagram of one embodiment of a computing system for a system for monitoring cardiac function of a patient.

FIG. 4 provides another system diagram of an exemplary embodiment of the computer system 200 for the system 1 for monitoring cardiac function of a patient 4 and which has a position analysis module 52 and a waveform analysis module 54 that operate as described herein. The computing system 200 generally includes a processor 206, storage system 204, software 202, communication interface 208 and a user interface 210. The processor 206 loads and executes software 202 from the storage system 204, including the position analysis module 52, and the waveform analysis module 54, which are applications within the software 202. Each of the modules 52 and 54 include computer-readable instructions that, when executed by the computing system 200 (including on the processor 206), direct the processor 206 to operate as described in herein in further detail, including to execute one or more of the steps described.

Although the computing system 200 as depicted in FIG. 4 includes one software element 202 encapsulating one position analysis module 52 and one waveform analysis module 54, it should be understood that one or more software elements having one or more modules may provide the same operation. Thus, the functions described herein as being performed by the respective modules 52 and 54 may be directed and executed by a single, combined module, or by many separate modules. Similarly, while description as provided herein refers to a computing system 200 and a processor 206, it is to be recognized that implementations of such systems can be performed using one or more processors, which may be communicatively connected, and such implementations are considered to be within the scope of the description. For example, the processor 206 may encompass a distributed processing system, such as in a cloud computing environment and system.

The processor 206 may comprise a microprocessor and other circuitry that retrieves and executes software 202 from storage system 204. Processor 206 can be implemented within a single processing device, but can also be distributed across multiple processing devices or sub-systems that cooperate in executing program instructions. Examples of processors 206 include general purpose central processing units, application-specific processors, and logic devices, as well as any other type of processing device, combinations of processing devices, or variations thereof.

The storage system 204, which includes the ECG database 20, can comprise any storage media, or group of storage media, readable by processing system 206 and/or capable of storing software 202. The storage system 204 can include volatile and non-volatile, removable and non-removable media implemented in any method or technology for storage of information, such as computer-readable instructions, data structures, program modules, or other data. Storage system 204 can be implemented as a single storage device but may also be implemented across multiple storage devices or sub-systems. For example, the software 202 may be stored on a separate storage device than the ECG database 20. Likewise, ECG database 20 can be stored, distributed, and/or implemented across one or more storage media or group of storage medias. Similarly, ECG database 20 may encompass multiple different sub-databases at different storage locations and/or containing different information which may be stored in different formats. By way of example, the ECG database 20 may encompass a MUSE ECG management system housing waveform data. Storage system 204 can further include additional elements, such a controller capable, of communicating with the processor system 206.

Examples of storage media include random access memory, read only memory, magnetic discs, optical discs, flash memory, virtual memory, and non-virtual memory, magnetic sets, magnetic tape, magnetic disc storage or other magnetic storage devices, or any other medium which can be used to storage the desired information and that may be accessed by an instruction execution system, as well as any combination or variation thereof, or any other type of storage medium. Likewise, the storage media may be housed locally with the processing system 206, or may be distributed in one or more servers, which may be at multiple locations and networked, such as in cloud computing applications and systems. In some implementations, the storage media can be a non-transitory storage media. In some implementations, at least a portion of the storage media may be transitory.

The communication interface 208 is configured to communicate with the ECG monitor 8 to receive the cardiac waveform data 52 for the patient, and to receive one position input 30 from the one or more position sensors 10. The user interface 210 may configured to receive input from a clinician, for example, and to output the cardiac status 38. The user interface 210 may also be configured to provide notification of an alarm condition 40. User interface 210 may include a mouse, a keyboard, a voice input device, a touch input device for receiving a gesture from a user, a motion input device for detecting non-touch gestures and other motions by a user, and other comparable input devices and associated processing elements capable of receiving user input from a user, such as a clinician. Output devices such as a video display or graphical display can display an interface further associated with embodiments of the system and method as disclosed herein and may display a visual depiction of the cardiac status 38 and/or the alarm condition notification 40. Speakers, printers, haptic devices and other types of output devices may also be included in the user interface 210, such as to provide an auditory notification of an alarm condition notification 40.

Figure 5:
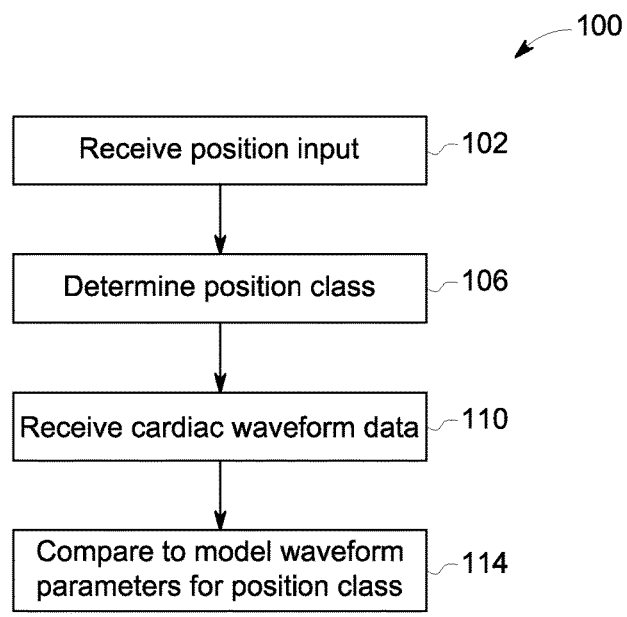
FIG. 5 depicts one embodiment of a method of monitoring cardiac function of a patient.

FIG. 5 depicts one embodiment of a method 100 of monitoring cardiac function of a patient. Position input is received at step 102, such as from one or more position sensors 10. The position class is determined based on the position input at step 106. At step 110, cardiac waveform data is received, such as directly or indirectly from an ECG monitor 8. At step 114, the cardiac waveform data is compared to model waveform parameters for the position class determined at step 106.

Figure 6:
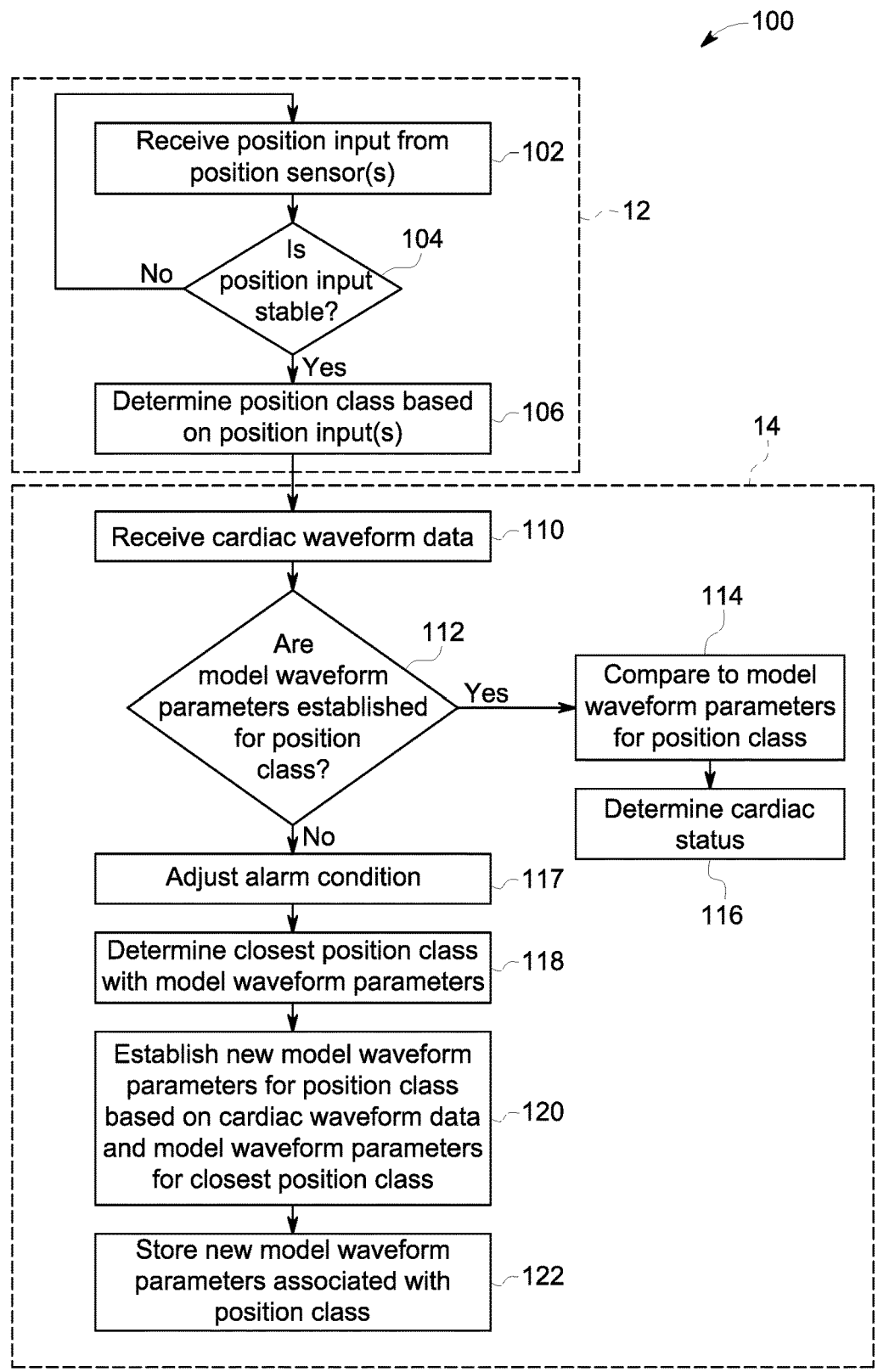
FIG. 6 depicts another embodiment of a method of monitoring cardiac function of a patient.

FIG. 6 depicts another embodiment of a method 100 of monitoring cardiac function of a patient. After position input is received from position sensors at step 102, the position analysis module 52 determines whether the position input is stable at step 104. For example, it may determine whether the position input received sequential outputs from the one or more position sensors are within a threshold value of one another, such as a predetermined number of inputs that fall within the same position class or within a predetermined angular range of one another. In another embodiment where multiple position sensors are utilized, the position input may be determined to be stable when the outputs of the position sensors are within a threshold range of one another. If the position input is not stable, then the position analysis module 52 may return to step 102 and monitor the position input until stability is reached. Once the position input is stable, the position analysis module 52 determines position class at step 106 based on the one or more position inputs. The position analysis module 52 may then output position class to the waveform analysis module 54. However, as is described above, in other embodiments, the method steps may all be executed by a single software module that determines position class and cardiac status.

At step 110, the waveform analysis module 54 receives the cardiac waveform data. It then determines at step 112 whether model waveform parameters are established for the position class determined at step 106. If model waveform parameters are available, then the waveform analysis module 54 compares the cardiac waveform data to the model waveform parameters at step 114, such as by comparing it to the average waveform established for the position class as is described above. The cardiac status is then determined at step 116 based on the results of the comparison. The waveform analysis module 54 may then output the cardiac status, such as to a clinician and/or to the ECG database 20. Additionally, as is described above, the waveform analysis module 54 may also assess whether alarm thresholds have been met.

Returning to step 112, if model waveform parameters have not been established for the position class, then the alarm condition parameters are adjusted at step 117. At step 118, the waveform analysis module 54 finds the closest position class for which model waveform parameters have been established and utilizes those parameters as a starting point for establishing the new model waveform parameters at step 120. The new model waveform parameters may be established based on the model waveform parameters for the closest position class and the cardiac waveform data received at step 110, such as by adjusting the model waveform parameters for the closest position class based on the differences between it and the cardiac waveform data. At step 122, the new model waveform parameters are stored in association with the position class, such as in the ECG database 20. Assuming that the patient position has not changed, the waveform analysis module 54 may then assess the cardiac status of the patient using the newly-established model waveform parameters, as described in steps 110 through 116 and according to the methods disclosed herein.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

I claim:

1. A method of monitoring cardiac function of a patient, the method comprising:
   receiving at a processor a position input from a position sensor attached to the patient;
   classifying the position input into a position class;
   based on the position class, accessing model cardiac waveform parameters associated with the position class, wherein the model cardiac wave form parameters establish a baseline when the patient's position is in the position class;
   receiving cardiac waveform data for the patient; and
   comparing the cardiac waveform data to the model cardiac waveform parameters associated with the position class.

2. The method of claim 1, wherein the position class is one of a predefined set of position classes.

3. The method of claim 2, wherein the predefined set of position classes includes at least a right side horizontal position, a left side horizontal position, a supine position, and a vertical position.

4. The method of claim 3, wherein the position input is classified into the closest one of the predefined set of position classes.

5. The method of claim 2, further comprising storing a set of model cardiac waveform parameters for each position class in the predefined set of position classes, wherein the model cardiac waveform parameters are based on cardiac waveform data recorded from the patient.

6. The method of claim 1, further comprising determining that the position input is stable prior to classifying the position input into a position class.

7. The method of claim 1, further comprising storing new model waveform parameters in association with the position class based on cardiac waveform data recorded from the patient.

8. The method of claim 7, further comprising determining a closest position class for which model waveform parameters are established, and establishing the new model waveform parameters for the position class based on the model waveform parameters for the closest position class.

9. The method of claim 7, further comprising adjusting one or more alarm conditions until the new model waveform parameters are established for the position class.

10. A system for monitoring cardiac function of a patient, the system comprising:
    an electrocardiograph monitor configured to record cardiac waveform data from the patient;
    at least one position sensor configured to sense a position of the patient and produce a position input;
    a processor;
    a position analysis module executable on the processor to:
      receive the position input;
      determine a position class based on the position input, wherein the position class is one of a predefined set of position classes;
      output the position class;
    a waveform analysis module executable on the processor to:
      receive the cardiac waveform data;
      identify appropriate model cardiac waveform parameters based on the position class wherein the model cardiac wave form parameters establish a baseline when the patient's position is in the position class;
      compare the cardiac waveform data to the model cardiac waveform parameters for the position class to determine a cardiac status of the patient; and
      output the cardiac status.

11. The system of claim 10, wherein the predefined set of position classes includes at least a right side horizontal position, a left side horizontal position, a supine position, and a vertical position.

12. The system of claim 11, wherein the position input is determined as the closest one of the predefined set of position classes.

13. The system of claim 12, wherein the position analysis module is further executable on the processor to determine that the position input is stable prior to classifying the position input into a position class.

14. The system of claim 11, wherein the waveform analysis module further comprises a set of model cardiac waveform parameters for each position class in the predefined set of position classes; and wherein identifying appropriate model cardiac waveform parameters includes selecting a set of model cardiac waveform parameters stored in association with the position class.

15. The system of claim 14, wherein the position sensor includes an accelerometer attachable to a torso of the patient, and wherein the system further comprises a second accelerometer attachable to the patient and configured to provide a second position input, wherein the position analysis module is further executable on the processor to receive the second position input and determine the position class based on the position input and the second position input.

16. The system of claim 10, wherein the waveform analysis module is further executable on the processor to establish new model cardiac waveform parameters for the position class based on cardiac waveform data recorded from the patient.

17. The system of claim 16, wherein the waveform analysis module is further executable on the processor to adjust one or more alarm conditions until the new model cardiac waveform parameters are established for the position class.

18. A non-transitory computer-readable medium having computer-executable instructions stored thereon, wherein the instructions include steps comprising:

receiving a position input from a position sensor attached to the patient;
classifying the position input into a position class, wherein the position class is one of a predefined set of position classes;
identifying appropriate model cardiac waveform parameters based on the position class wherein the model cardiac wave form parameters establish a baseline when the patient's position is in the position class;
receiving cardiac waveform data for the patient; and
comparing the cardiac waveform data to model cardiac waveform parameters for the position class.

19. The non-transitory computer-readable medium of claim 18, wherein the instructions include the steps further comprising accessing a database comprising a set of model cardiac waveform parameters for each position class in the predefined set of position classes, and wherein identifying appropriate model cardiac waveform parameters includes selecting a set of model cardiac waveform parameters from the database based the position class.

20. The non-transitory computer-readable medium of claim 18, wherein the instructions include the steps further comprising establishing new model cardiac waveform parameters for the position class based on cardiac waveform data recorded from the patient.

* * * * *